(12) United States Patent
Carr

(10) Patent No.: US 8,123,725 B2
(45) Date of Patent: Feb. 28, 2012

(54) PORTABLE INFUSION PUMP OF THE SKIN PATCH TYPE WITH SPIRAL COLLAPSIBLE RESERVOIR

(75) Inventor: Matthew John Carr, Cambridge (GB)

(73) Assignee: The Technology Partnership PLC, Royston, Hertfordshire (GB)

( * ) Notice: Subject to any disclaimer, the term of this patent is extended or adjusted under 35 U.S.C. 154(b) by 236 days.

(21) Appl. No.: 12/282,940

(22) PCT Filed: Mar. 14, 2007

(86) PCT No.: PCT/GB2007/050123
§ 371 (c)(1),
(2), (4) Date: Oct. 26, 2009

(87) PCT Pub. No.: WO2007/107786
PCT Pub. Date: Sep. 27, 2007

(65) Prior Publication Data
US 2010/0168672 A1  Jul. 1, 2010

(30) Foreign Application Priority Data
Mar. 22, 2006 (GB) ................... 0605763.2

(51) Int. Cl.
*A61M 5/14* (2006.01)
(52) U.S. Cl. .................. 604/135; 604/131; 604/153
(58) Field of Classification Search .................. 604/151, 604/153, 154, 131, 135; 222/74, 75, 92, 222/94, 95, 98, 99, 10
See application file for complete search history.

(56) References Cited

U.S. PATENT DOCUMENTS

| 4,525,164 A * | 6/1985 | Loeb et al. ............... 604/131 |
| 4,734,092 A | 3/1988 | Millerd |
| 6,375,638 B2 | 4/2002 | Nason et al. |
| 7,178,692 B2 * | 2/2007 | Ophardt ................. 222/104 |
| 2005/0277887 A1 | 12/2005 | Douglas et al. |

FOREIGN PATENT DOCUMENTS

| WO | WO95/04561 | 2/1995 |
| WO | WO 9504561 A1 * | 2/1995 |

* cited by examiner

*Primary Examiner* — Laura Bouchelle

(57) ABSTRACT

An ambulatory pump comprising a reservoir (1) for holding the fluid to be pumped and having an outlet (7) through which fluid is expelled in use; a closure (8) device movable relative to the reservoir; and an actuator (14) for moving the closure device relative to the reservoir, wherein the reservoir is arranged in a spiral pattern.

15 Claims, 6 Drawing Sheets

PORTABLE INFUSION PUMP OF THE SKIN PATCH TYPE WITH SPIRAL COLLAPSIBLE RESERVOIR

The present invention relates to an ambulatory pump and, in particular to an ambulatory pump for transdermal drug delivery that can be worn on the surface of the skin of a patient. By "ambulatory pump", we mean one which enables the user to move around easily with the pump attached.

Many therapeutic agents sensitive to degradation in the digestive track require parenteral administration, commonly achieved by subcutaneous bolus injection. Whilst this method is both convenient and effective for a number of agents, the inherent limitation in tolerable bolus volume and in delivery frequency render it unsuitable for a growing class of therapeutics. A number of alternative delivery methods exist, including simple gravity fed infusion systems, transdermal patches and the motor driven cartridge systems common in both point-of-care and ambulatory delivery applications. However, these approaches each suffer from one or more limitations.

Gravity fed systems limit the therapy to simplistic flow rate and profiles and hinder patient mobility in use, given their size and requirement to have a particular orientation. In prior art infusion systems, a cartridge reservoir is typically employed with a moving plunger. In this configuration, it is necessary to control the position of the plunger to within the order of a few microns, due to the large bore of the cartridge and the minimum delivered volume or precision required. In addition, the geometry of the cartridge is susceptible to bubble entrapment problems, commonly accounted during the filling process.

Transdermal patches are found niche applications, but these are limited due to the molecular structure of the drug required for transdermal transport and the inherent variability in delivery rates associated with a diffusion limited process.

The delivery of insulin in the management of diabetes mellitus is a common application for miniaturised motor driven ambulatory pumps. Typically these devices incorporate drive electronics, a motor, a gear box and a lead screw to advance a plunger within a cartridge containing insulin. These devices are programmable, thereby allowing bolus volumes and basal profile to be controlled. However, existing devices of this sort cannot be worn on the skin due to the shear size and weight of the device. Furthermore, they are expensive, difficult to fill and require maintenance in the longer term. In addition, the volume dispensed for a given linear displacement tends to be high, given the size, and therefore these devices are not practical for dispensing small volumes.

Despite the marked benefits of infusion for a number of therapies, the use of bolus injection persists. There is, therefore, a clear need for a low cost, disposable, compact, skin-worn transdermal delivery device for delivering various therapeutics including, but not limited to, insulin, chemotherapeutics, analgesics, morphine, hormones, gene therapies and coagulants, antibiotics, cardiovascular medications, nutritional fluids and AZT.

One example of a known medication delivery device is shown in U.S. Pat. No. 6,375,638 in which a shape memory alloy wire is used to operate an incremental motion and drive mechanism, for example, one which is similar to the friction type motion used in car jacks and "squeeze grip" types of woodwork clamps. However, this document teaches only circular or linear motion of an actuator for dispensing fluid and this means that there is a relatively short length of tube which means that less fluid can be stored in the reservoir. In addition, the actuating mechanism uses a friction based indexing mechanism and this is inherently sensitive to changes in material properties and contact geometry, such that the accuracy of dispensing fluid can easily be adversely effective.

Thus, according to the present invention, there is provided an ambulatory pump comprising:
a reservoir for holding the fluid to be pumped and having an outlet through which fluid is expelled in use;
a closure device movable relative to the reservoir; and
an actuator for moving the closure device relative to the reservoir,
wherein the reservoir is arranged in a spiral pattern.

Thus, the present invention provides a spiral pattern reservoir which ensures that the necessary volume of fluid can be stored in a smaller device, thereby minimising the size and weight of the resulting pump. In addition, because of the high aspect ratios that can be used due to the spiral nature of the reservoir, the present invention overcomes the requirement for high resolution linear displacement and avoids many of the bubble entrapment issues common in the existing devices.

The reservoir preferably consists of a long length of flexible tubing with a small internal diameter, typically of the order of 0.1 to 2 mm, and is preferably formed in an archimedian spiral, thereby minimising the space envelope required for a reservoir of a given volume. The reservoir is preferably open at one end and is terminated by an outlet which can, in use, be connected to a transcutaneous cannula. The closure is configured both to collapse the tube and also preferably to incrementally advance it along the reservoir towards the outlet, thereby displacing fluid towards and through the outlet.

The aspect ratio of the reservoir, defined as the ratio of the internal diameter of the reservoir to its length, is preferably of the order of 100 to 10000, as this significantly increases the linear displacement of the closure per unit volume dispensed, thereby reducing the required positional resolution of the closure relative to that of the plunger common in existing systems.

Since the present invention does not require recovery of the tube geometry, the material from which the flexible tube is formed, such as PTFE (polytetrafluoroethylene), PP (polypropylene) or PE (polyethylene), can be of low resilience or even not resilient and therefore the force required to collapse the tube can be correspondingly low compared with existing peristaltic delivery systems. This in turn improves the energy efficiency of the device and can help reduce its size. Additionally, the use of a relatively inelastic tube reduces the need for plasticisers in the polymer formulation. This in turn improves drug compatibility, as plasticisers are often extractable by many drug formulations and therefore, by avoiding their use, a greater number of formulations can be delivered.

The closure device preferably experiences a smaller frictional force when moving towards rather than away from the outlet and this may be achieved by providing a leg extending rearwardly from the closure, such that the leg contacts the outer surface of the reservoir in use. In addition, or alternatively, the pump may be provided with a ratchet mechanism which engages with the closure device to permit travel towards the outlet only. By "towards" the outlet, we mean that the closure move along the reservoir such that the distance along the reservoir from the closure to the outlet is reduced. For example, when the reservoir is a spiral, the closure moves along the reservoir following the spiral, but does not travel directly towards the outlet. Such movement falls within the term "towards".

The actuator is preferably an oscillatory actuator and the rotational movement of the actuator is preferably limited such that the closure element can only move a predetermined amount for any single actuation. This predetermined amount is preferably the pitch of the driving teeth during any single actuation. The actuator preferably includes a series of teeth which engage with a corresponding portion of the closure device such that rotation of the actuator causes a tooth to drive the closure device along the reservoir towards the outlet, thereby expelling fluid from the reservoir.

The teeth are preferably arranged on the actuator in a spiral pattern to correspond to the spiral pattern of the reservoir, thereby enabling the closure device to "follow" the reservoir during multiple actuations.

The actuator preferably consists of a shape memory alloy (SMA) wire and a biasing means for returning the SMA wire to its original state following actuation. Actuation is achieved by resistively heating the SMA wire until it reaches transformation temperature, at which point the wire returns to its shorter memorised state. The biasing means could be a spring or a second SMA wire functioning in a similar manner to that described above.

One example of the present invention will now be described with reference to the accompanying drawings, in which.

Figure 1:
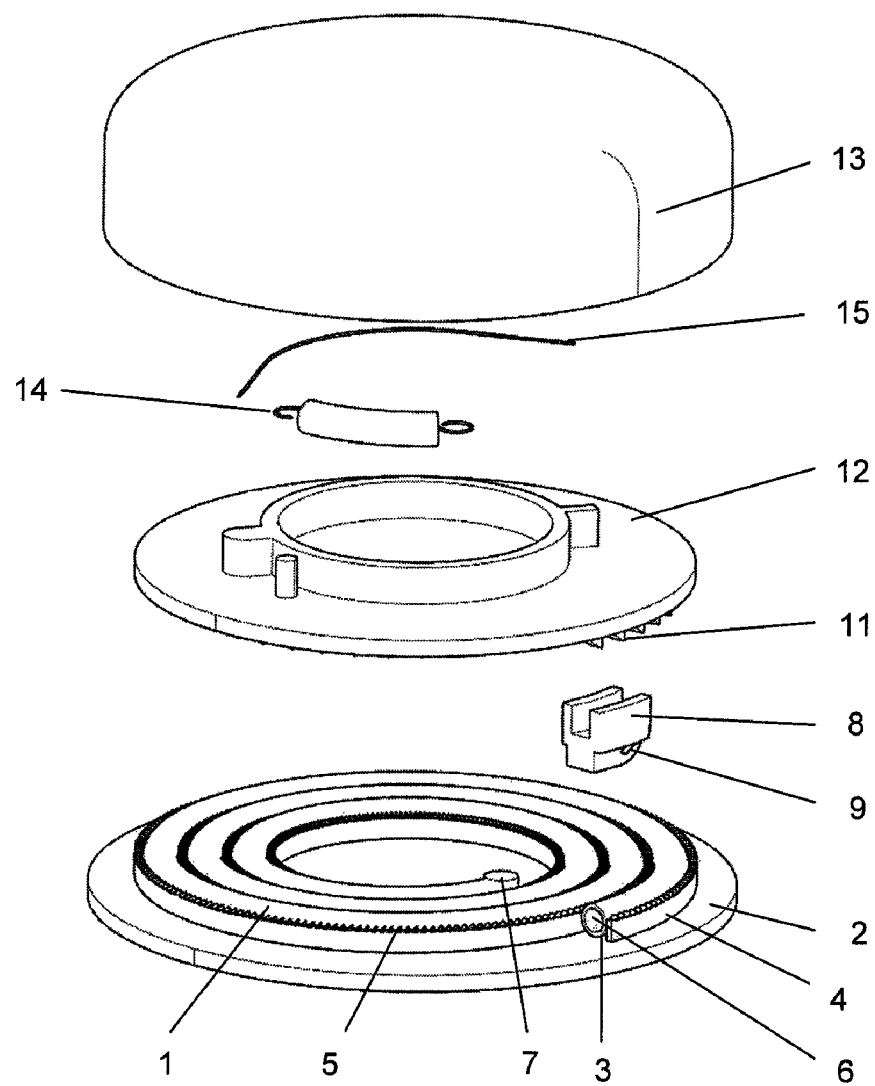
FIG. 1 shows an exploded view from above and one side of one example of the present invention.
Figure 2:
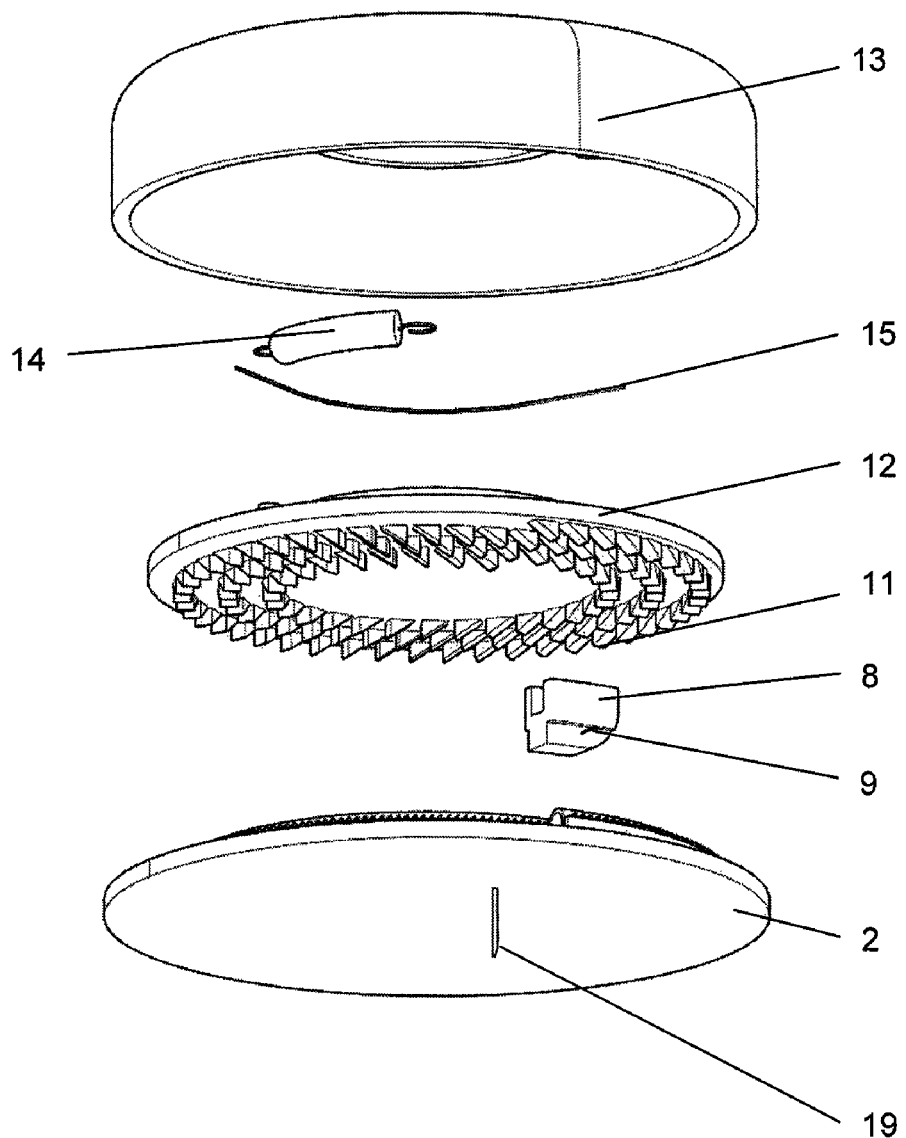
FIG. 2 shows an exploded view from below of the device of FIG. 1.
Figure 3:
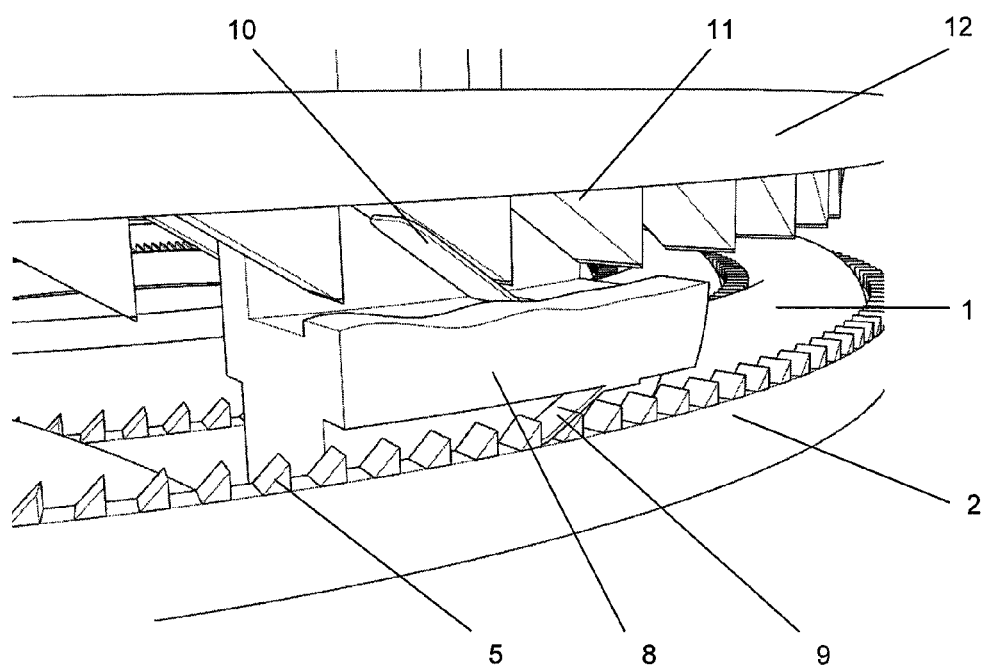
FIG. 3 shows a close up view of the closure device when the pump is constructed.

FIGS. 1 to 3 show an embodiment of the present invention. An elongate, tubular reservoir 1 is mounted on a base 2 which has a channel 3 defined by a spiral upstanding wall 4 having, on its upper surface, a series of teeth 5. The reservoir is open at its outermost end 6 and is terminated at an outlet 7 to which a transcutaneous cannula 19 (see FIG. 2) can be attached. The reservoir may alternatively be defined by the upstanding wall 4 and have an elastic membrane (not shown) providing a top to the reservoir. A closure device 8 has one or more teeth 9 which engage with the teeth 5 formed on the base 2 to prevent movement of the closure 8 towards the outermost end of the reservoir 1. The closure also has one or more teeth 10 which engage with corresponding driving teeth 11 formed in a spiral, that substantially corresponds to the spiral of the reservoir, on the underside of a drive plate 12. The drive plate is connected to a cap 13 by means of a return spring 14 and a shape memory alloy wire 15, such that rotation of the cap 13 causes the drive plate to rotate.

In use, the reservoir 1 is filled from a conventional syringe which can be connected to the open end 6. Due to the small internal diameter of the tube, surface tension acts to maintain a continuous fluid front, preventing air entrapment as the fluid front advances from the open end 6 towards the outlet 7 during the filling processing. Fluid is dispensed from the reservoir 1 by first collapsing the reservoir 1 with the closure 8 and then moving the closure along the tube away from the open end 6. The closure is advanced along the tube under the action of driving teeth 11 disposed around a matching archimedian spiral on the underside of drive plate 12. The closure 8 is constrained such that it can only move away from the open end 6 of the tube either by engagement with small teeth 5 acting in the opposite direction to the driving teeth 11, or by asymmetric friction force developed by a sprag-like mechanism shown in FIGS. 5 and 6.

In order to reduce friction between the closure and the tube, a rotating element on the closure, or a rotary closure itself, can be employed similar to those found in conventional peristaltic systems. This could replace the sliding interface between the reservoir tube and the movable, thereby reducing friction and improving the mechanical efficiency of the device.

Figure 4:
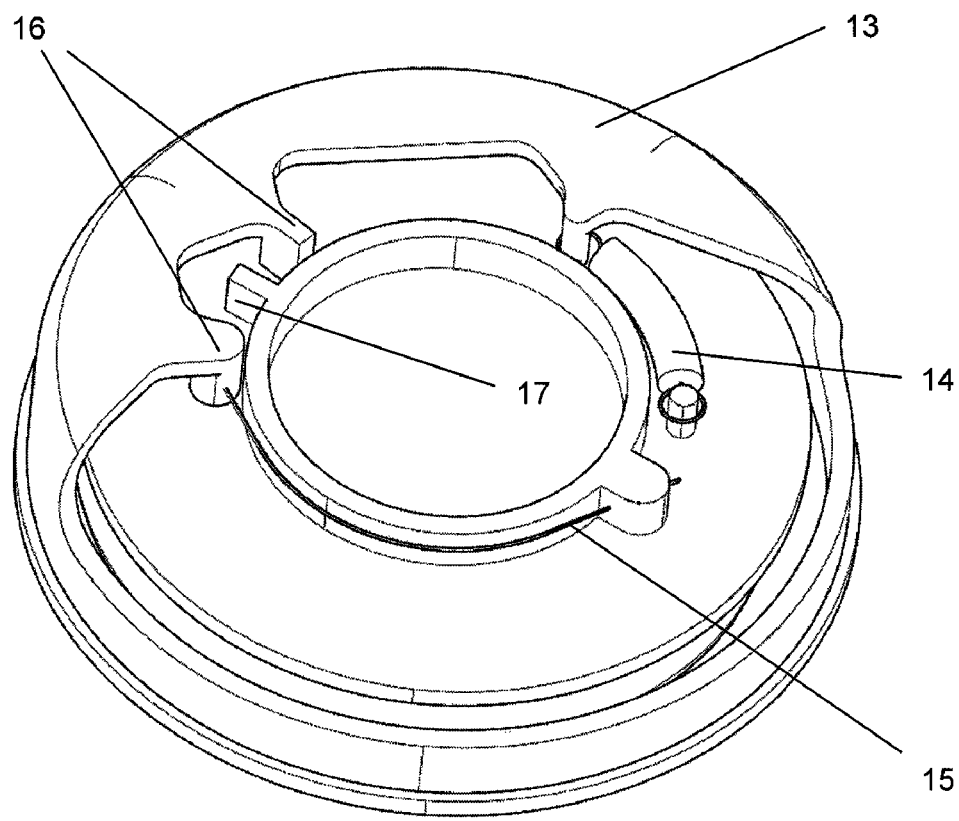
FIG. 4 shows a partially cut through, perspective view of the device of FIG. 1 from above.

The tooth spiral on the underside of the drive plates 12 is driven in an oscillatory fashion by means of the actuation arrangement shown in FIG. 4.

A cap 13 is provided over drive plate 12 and projections 16 extend inwardly from the cap portion to engage with a corresponding projection 17 on the drive plate 12. Thus, rotation of the cap relative to the drive plate will bring one of the projections 16 into contact with projection 17, thereby causing the drive plate to be rotated in the appropriate direction.

The drive plate 12 is caused to move between the limiting features 11 by the shape memory alloy wire 15 and the return spring 14. Actuation is achieved by resistively heating the SMA wire 15 until it reaches transformation temperature, at which point the wire 15 returns to its shorter memorised state, thereby causing the drive plate 12 to rotate relative to the cap 13. The return spring 14, or a second SMA wire functioning in a similar manner to that described above but in the opposite direction, can be used to rotate the drive plate relative to the cap in the opposite direction after the actuation has occurred. The drive plate 12 is constrained by the cap such that it is free to rotate between the limiting features 16, but is prevented from moving in any of the remaining degrees of freedom.

The tooth spiral 11 can be driven in an oscillatory fashion and engages with the closure 8 such that the closure advances only by the pitch of the tooth spiral 11 during each cycle of motion. The required angle of the rotary oscillation is of the order of a few degrees and, as such, it can be driven by simple actuation means such as the shape memory alloy wire 15. The angle of maximum rotary oscillation is fixed by the projections 16 and therefore the circumferential displacement of any particular tooth 11 on the drive wheel 12 is proportional to its radial position. To ensure that the movable closure 8 never moves more than a single tooth pitch, the radial position of the innermost tooth must be greater than half of the radial position of the outermost tooth and the pitch of the teeth must be less than the product of the oscillatory angle measured in Radians and the radial position of the innermost tooth. This ensures that the movement of the outermost driving tooth is not sufficient for the closure to move more than a distance equal to the pitch of the driving teeth during a single actuation cycle.

Figure 5:
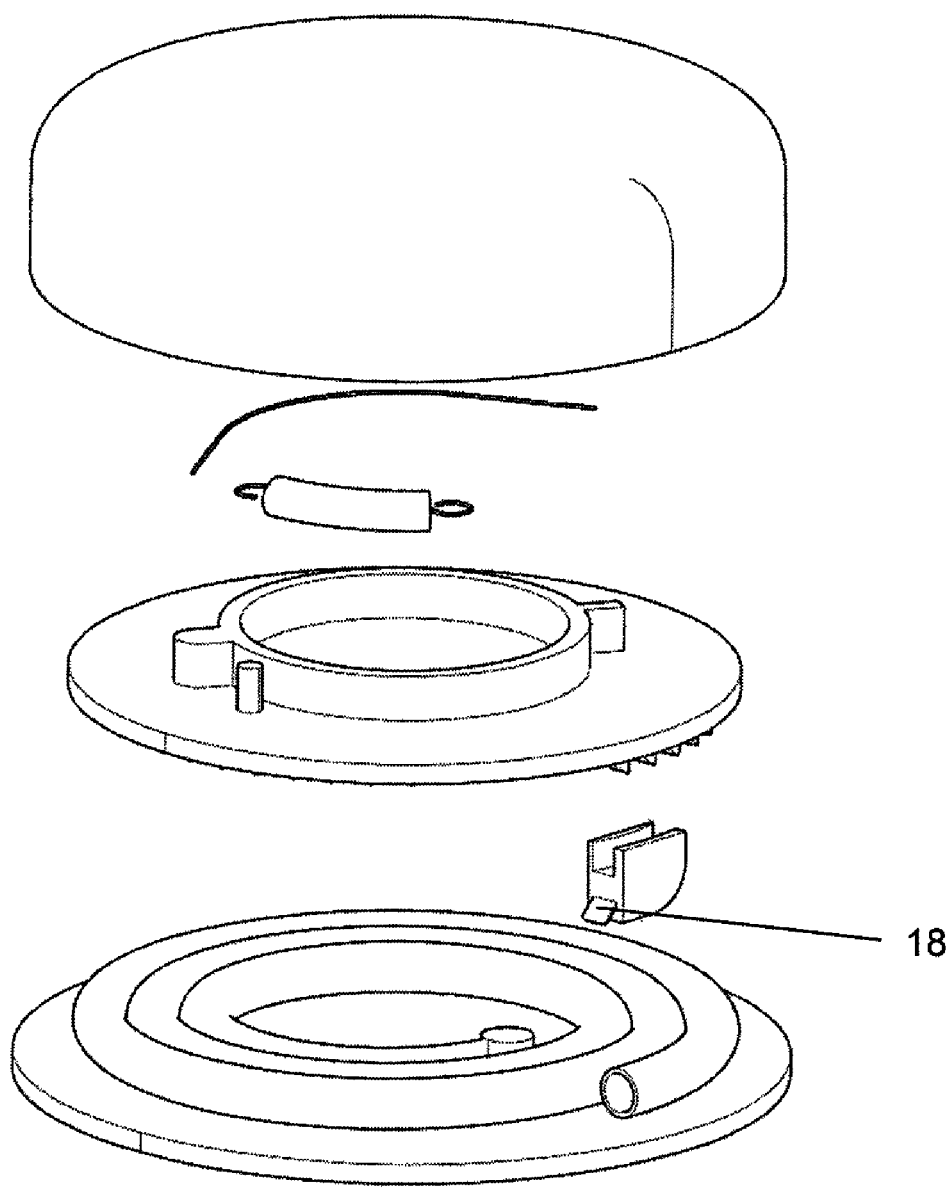
FIGS. 5 and 6 show a rearwardly extending leg on the closure element.
Figure 6:
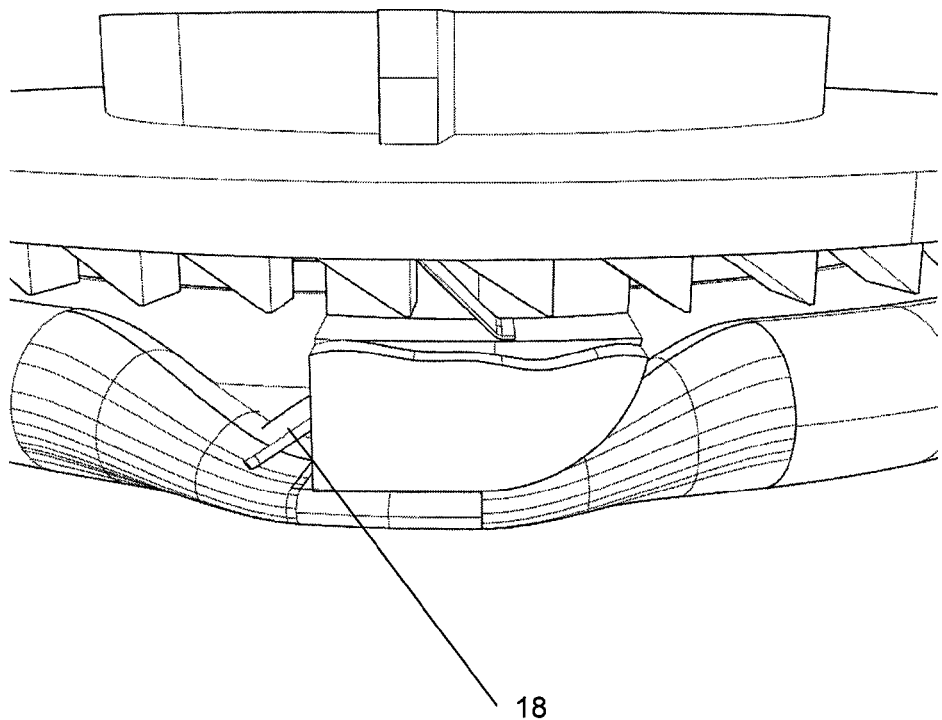

FIGS. 5 and 6 show an alternative arrangement for preventing the closure 8 from moving towards the open end 6. In this embodiment, a leg 18 bears against the reservoir 1 such that a reaction force can be developed to oppose forces acting in the direction of the outermost end 6. In this configuration, it is possible to reduce the volume that the reservoir occupies as there is no need for the teeth 5 or the upstanding wall 4, thus allowing the reservoir coils to be more closely packed.

The invention claimed is:

1. An ambulatory pump for dispensing fluid to be pumped through a transcutaneous cannula comprising:
   a reservoir comprising a relatively long length of flexible tubing arranged in a spiral pattern for holding the fluid to be pumped and having an outlet through which fluid is expelled in use;
   a closure device disposed external to the flexible tubing and engaging an exterior surface thereof, said closure device being discretely movable relative to the flexible tubing forming the reservoir for crushing the reservoir; and an actuator for moving the closure device incrementally relative to the reservoir.

2. A pump according to claim 1, wherein the closure device is configured to contact the outside of the reservoir such that movement of the closure device towards the outlet of the reservoir crushes part of the reservoir, thereby causing fluid to be expelled from the reservoir.

3. A pump according to claim 1, wherein the closure device experiences a smaller frictional force when moving towards rather than away from the outlet.

4. A pump according to claim 1, wherein the closure device is configured such that, in use, it is only movable towards the fluid to expel fluid from the reservoir.

5. A pump according to claim 1, wherein the closure device further comprises a leg extending rearwardly from the closure such that the leg contacts the outer surface of the reservoir.

6. A pump according to claim 1, further comprising a ratchet mechanism which engages with the closure device to permit travel only towards the outlet.

7. A pump according to claim 1, wherein the reservoir comprises a flexible tube.

8. A pump according to claim 7, wherein the reservoir has an aspect ratio of between 100 and 10000.

9. A pump according to claim 1, wherein the spiral is Archimedean.

10. A pump according to claim 1, wherein the reservoir is formed from a non-resilient material.

11. A pump according to claim 1, wherein the actuator includes a shape memory alloy element for causing the closure device to move relative to the reservoir and thereby expel fluid from the reservoir.

12. A pump according to claim 1, wherein the actuator is oscillatory.

13. A pump according to claim 12, wherein the rotational movement of the oscillatory actuator is limited such that the closure element can only move a predetermined amount for any single actuation.

14. A pump according to claim 12, wherein the oscillatory actuator returns to its rest position by means of a biasing means.

15. A pump according to claim 14, wherein the biasing means includes at least one of the following: a spring or a shape memory alloy wire.

* * * * *